US007577478B1

(12) United States Patent
Kroll et al.

(10) Patent No.: US 7,577,478 B1
(45) Date of Patent: Aug. 18, 2009

(54) ISCHEMIA DETECTION FOR ANTI-ARRHYTHMIA THERAPY

(75) Inventors: Mark W. Kroll, Crystal Bay, MN (US); Peter Boileau, Valencia, CA (US); Jong Gill, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 549 days.

(21) Appl. No.: 11/346,859

(22) Filed: Feb. 1, 2006

(51) Int. Cl.
*A61N 1/39* (2006.01)

(52) U.S. Cl. .......................... 607/6; 600/485; 600/513; 600/549

(58) Field of Classification Search ................... 607/21, 607/14, 18, 5–8; 600/526
See application file for complete search history.

(56) References Cited

U.S. PATENT DOCUMENTS

| | | | | |
|---|---|---|---|---|
| 4,712,555 | A | 12/1987 | Thornander et al. | 128/419 PG |
| 4,788,980 | A | 12/1988 | Mann et al. | 128/419 PG |
| 4,940,052 | A | 7/1990 | Mann et al. | 128/419 PG |
| 5,306,293 | A * | 4/1994 | Zacouto | 607/17 |
| 5,466,254 | A | 11/1995 | Helland | 607/123 |
| 5,476,483 | A | 12/1995 | Bornzin et al. | 607/17 |
| 5,531,768 | A | 7/1996 | Alferness | 607/6 |
| 6,314,323 | B1 | 11/2001 | Ekwall | 607/23 |
| 6,501,983 | B1 * | 12/2002 | Natarajan et al. | 600/517 |
| 6,514,195 | B1 | 2/2003 | Ferek-Petric | 600/17 |
| 6,604,000 | B2 | 8/2003 | Lu | 607/17 |
| 2002/0120205 | A1 | 8/2002 | Ferek-Petric | 600/513 |
| 2005/0004476 | A1 | 1/2005 | Payvar et al. | 600/481 |

FOREIGN PATENT DOCUMENTS

EP 0 728 498 B1 9/2004

OTHER PUBLICATIONS

Tetsuo Shioi, MD, PhD et al., "*Rapamycin Attenuates Load-Induced Cardiac Hypertrophy in Mice*," Circulation. 2003; 107:1664-1670.
Sitabhra Sinha et al., "Critical Role of Inhomogeneities in Pacing Termination of Cardiac Reentry," *Chaos*, vol. 12, No. 3 (Sep. 2002), pp. 893-902.
Christodoulous Stefanadis, MD et al., "*Cooling Effect of Coronary Blood Flow on Heart: A New Approach*," J. Invas Cardiol 2004; 16:455-458.
James N. Weiss et al., "*Ventricular Fibrillation—How Do We Stop the Waves From Breaking?*" Circ Res. 2000; 87:1103-1107.

* cited by examiner

Primary Examiner—Mark W Bockelman
Assistant Examiner—Elizabeth So

(57) ABSTRACT

An exemplary method includes detecting arrhythmia, detecting myocardial ischemia, determining whether the myocardial ischemia comprises local ischemia or global ischemia and, in response to the determining, calling for delivery of either a local ischemic anti-arrhythmia therapy or a global ischemic anti-arrhythmia therapy. Various other exemplary methods, devices, systems, etc., are also disclosed.

6 Claims, 10 Drawing Sheets

Exemplary Method 400

EXEMPLARY CORONARY SINUS FLOW
710

EXEMPLARY MEASUREMENT TIMING
740

EXEMPLARY TABLE OF PARAMETERS AND LOCATIONS
810

| VESSEL/ STRUCTURE | T | $O_2$ | PH | DV/DT | PRESS. |
|---|---|---|---|---|---|
| GCV | | | | | |
| LMV | | | | | |
| MCV | | | | | |
| PV | | | | | |
| LAV | | | | | |
| OSTIUM | | | | | |
| CS | | | | | |
| RV | | | | | |
| IVC/SVC | | | | | |

EXEMPLARY PLOT OF INTER-CORONARY SINUS PARAMETER VERSUS TIME
840

ISCHEMIA DETECTION FOR ANTI-ARRHYTHMIA THERAPY

TECHNICAL FIELD

Subject matter presented herein generally relates to detection of ischemia and treatment of arrhythmia. Various exemplary methods, devices, systems, etc., concern use of an implantable device to aid in detection of ischemia and to deliver anti-arrhythmia therapy.

BACKGROUND

Implantable devices that deliver anti-arrhythmia therapy save lives. Typical types of anti-arrhythmia therapy include anti-tachycardia pacing therapy, cardioversion shock therapy and defibrillation shock therapy. In general, such therapies are implemented in response to detection of an arrhythmia. Many implantable devices detect and classify arrhythmia and then respond based on the classification. For example, ATP therapy may be delivered in response to classification of an arrhythmia as a tachycardia while defibrillation shock therapy may be delivered in response to classification of an arrhythmia as fibrillation. While such therapies have proven successful, success is not guaranteed; thus, a need for improved therapies exists.

Various exemplary methods, devices, systems, etc., described herein acquire information pertaining to ischemia and use such information in determining an appropriate anti-arrhythmia therapy. Ischemia is a condition resulting from insufficient myocardial blood flow, which may be a consequence of arrhythmia or a cause of arrhythmia. Further, ischemia can contribute to worsening of an arrhythmia. Thus, if ischemia is present, information pertaining to ischemia can aid in selecting or adjusting anti-arrhythmia therapy. Other exemplary methods, devices, systems, etc., are also disclosed.

SUMMARY

An exemplary method includes detecting arrhythmia, detecting myocardial ischemia, determining whether the myocardial ischemia comprises local ischemia or global ischemia and, in response to the determining, calling for delivery of either a local ischemic anti-arrhythmia therapy or a global ischemic anti-arrhythmia therapy. Various other exemplary methods, devices, systems, etc., are also disclosed.

In general, the various methods, devices, systems, etc., described herein, and equivalents thereof, are optionally suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

Various exemplary methods, devices, systems, etc., described herein pertain to acquiring information related to ischemia and optionally using such information to determine appropriate therapy. For example, anti-arrhythmia therapy may be adjusted based on the presence of ischemia and optionally on whether the ischemia, if present, is global or local. An exemplary implantable cardiac therapy device is described below that may acquire ischemia information and delivery anti-arrhythmia therapy. In various examples, ischemia information is optionally used for arrhythmia detection.

Exemplary Stimulation Device

The techniques described below are optionally implemented in connection with any stimulation device that is configured or configurable to stimulate and/or shock tissue.

Figure 1:
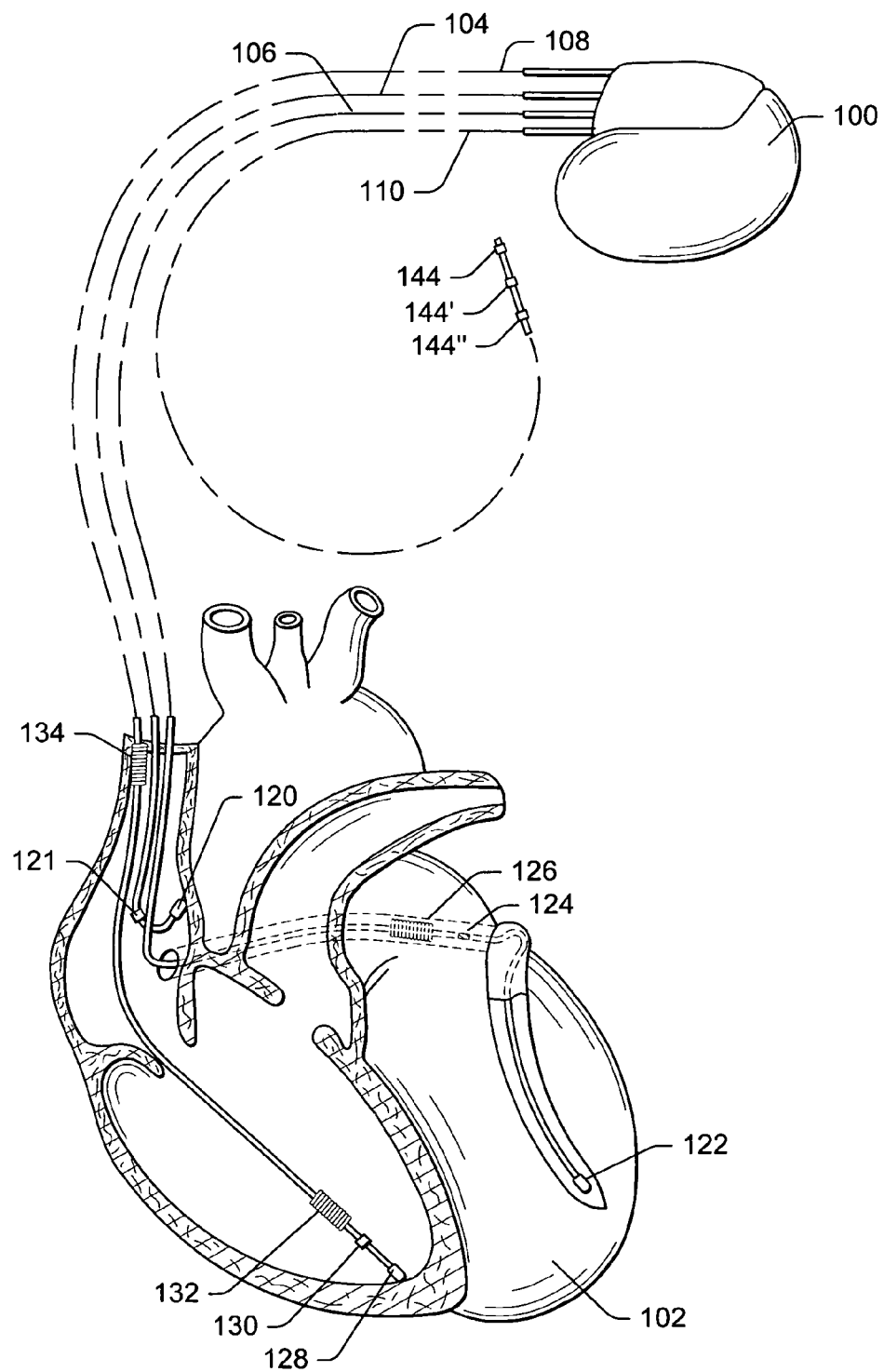
FIG. 1 is a simplified diagram illustrating an exemplary implantable stimulation device in electrical communication with at least three leads implanted into a patient's heart and at least one other lead for delivering stimulation and/or shock therapy. The exemplary stimulation device optionally includes one or more sensors for sensing physiologic conditions (e.g., blood flow, pressure, etc.).

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves, non-myocardial tissue, other nerves, etc. In addition, the device 100 includes a fourth lead 110 having, in this implementation, three electrodes 144, 144', 144" suitable for stimulation of autonomic nerves, non-myocardial tissue, other nerves, etc. For example, this lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves, non-myocardial tissue, other nerves, etc.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus (CS) include, but may not be limited to, the great cardiac vein (GCV), the left marginal vein (LMV), the left posterior ventricular vein (PV), the middle cardiac vein (MCV), and the small cardiac vein (SCV).

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of such a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, non-myocardial tissue, other nerves, etc., wherein such an electrode may be positioned on the lead or a bifurcation or leg of the lead. Other exemplary coronary sinus leads are discussed below (see, e.g., FIGS. 6 and 9).

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, non-myocardial tissue, other nerves, etc., wherein such an electrode may be positioned on the lead or a bifurcation or leg of the lead.

Figure 2:
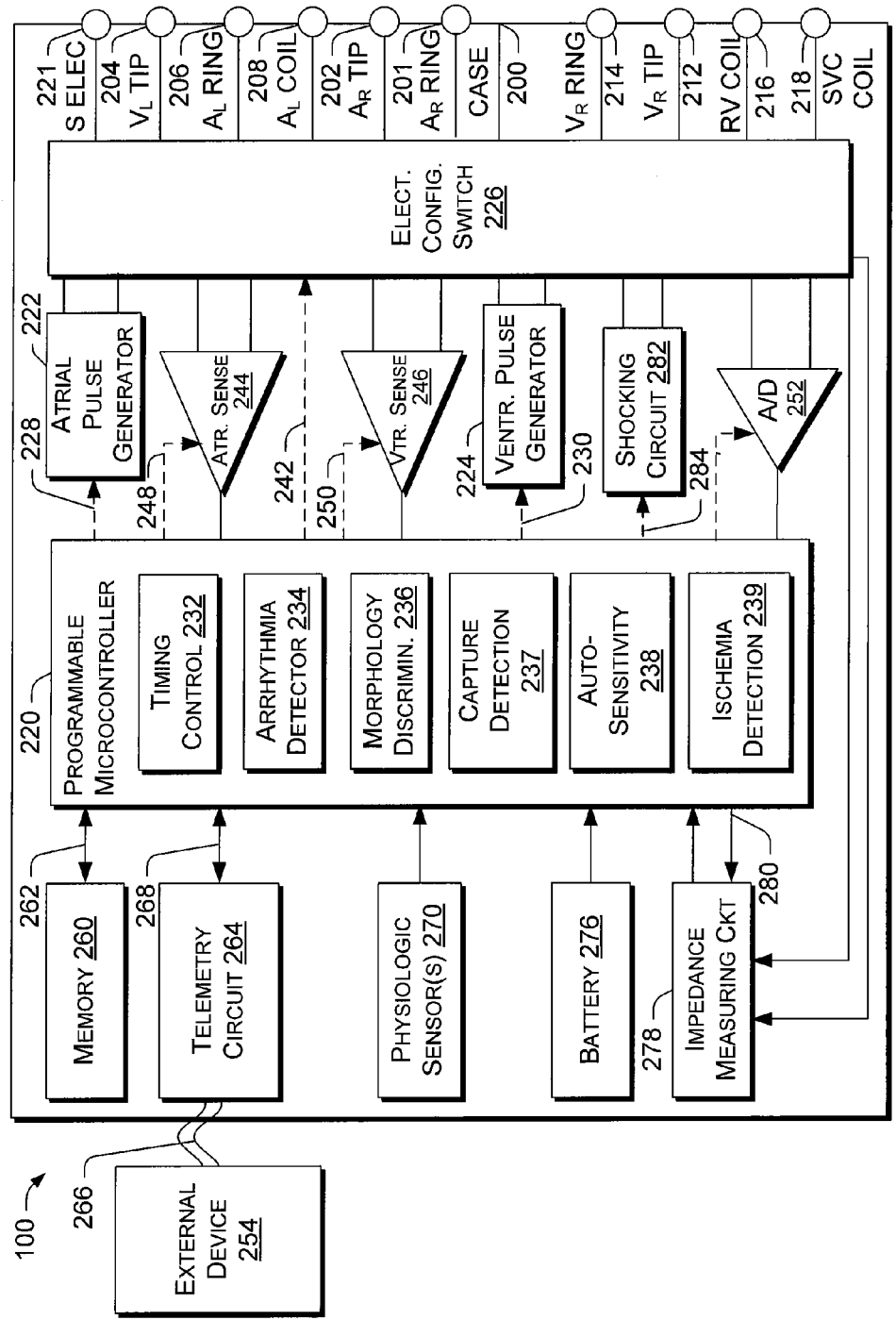
FIG. 2 is a functional block diagram of an exemplary implantable stimulation device illustrating basic elements that are configured to provide cardioversion, defibrillation, pacing stimulation or other tissue or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves, non-myocardial tissue, other nerves, etc. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, autonomic nerve stimulation, non-myocardial tissue stimulation, other nerve stimulation, etc.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing and/or pacing, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

To support right chamber sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes or other tissue stimulation or sensing electrodes is also possible via these and/or other terminals (e.g., via a nerve and/or tissue stimulation and/or sensing terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology discrimination module 236, a capture detection module 237, an auto sensitivity module 238, an ischemia detection module 239 and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The ischemia detection module 239 may perform a variety of tasks related to, for example, detection of ischemia. This component can be used by the stimulation device 100 in determining therapy in response to ischemia information. The ischemia detection module 239 may be implemented in hardware as part of the microcontroller 220, or as software/firmware instructions programmed into the device and executed on the microcontroller 220 during certain modes of operation. The ischemia detection module 239 may optionally implement various exemplary methods described herein. The ischemia detection module 239 may interact with one or more physiological sensors 270, the impedance measuring circuit 278 and optionally other modules.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, etc.) are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve or other tissue stimulation lead 110 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

As already mentioned, the stimulation device 100 can further include or communicate with one or more physiologic sensors 270. The physiologic sensors 270 may be housed within the case 200, on the surface of the case 200 or external to the case 200. The one or more physiologic sensors optionally connect to the device 100 via one or more of the connectors or via other connectors. In some instances, a physiologic sensor may communicate with the microcontroller 220 via a wireless link. For example, a wristwatch physiologic sensor may communicate via electromagnetic radiation signals or other signals with a circuit in the device 100 (e.g., the telemetry circuit 264). Of course, an implantable physiologic sensor may also communicate with the device 100 via such communication means.

As described herein, ischemia may be detectable by various changes in physiology and hence by any of a variety of physiologic sensors, which can include use of aforementioned stimulation leads 104, 106, 108, 110 as electrical activity sensors. Ischemia may be detectable based on temperature changes, decreased local myocardial pressure, decreased myocardial pH, decreased myocardial $pO_2$, increased myocardial $pCO_2$, increased myocardial lactate, increased ratio of lactate to pyruvate in the myocardium, increased ratio of the reduced form of nicotine amide adenine dinucleotide (NADH) to nicotine amide adenine dinucleotide ($NAD^+$) in the myocardium, increased ratio of the reduced form of nicotinamine-adenine dinucleotide phosphate (NADPH) to nicotinamine-adenine dinucleotide phosphate (NADPH) in the myocardium, increased ST segment, decreased ST segment, ventricular tachycardia, T wave changes, QRS changes, decreased patient activity, increased respiratory rate, decreased transthoracic impedance, decreased cardiac output, increased pulmonary artery diastolic pressure, increased myocardial creatinine kinase, increased troponin, and changed myocardial wall motion. Sensed information pertaining to ischemia as well as exemplary mechanisms for sensing such information is discussed in more detail below.

With respect to pressure sensors, commercially available pressure transducers include those marketed by Millar Instruments (Houston, Tex.) under the mark MIKROTIP®. A study by Shioi et al., "Rapamycin Attenuates Load-induced Cardiac Hypertrophy in Mice", *Circulation* 2003; 107:1664, measured left ventricular pressures in mice using a Millar pressure transducer inserted through the LV apex and secured in the LV apex with a purse-string suture using 5-0 silk. Various exemplary methods, devices, systems, etc., described herein optionally use such a pressure transducer to measure pressures in the body (e.g., chamber of heart, vessel, etc.).

A physiologic sensor may be used to implement "rate-responsive" therapy where information sensed is used to adjust pacing stimulation rate according to, for example, the exercise state of the patient. A physiological sensor may be used to sense changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). The microcontroller 220 can respond to such information by adjusting any of the various pacing parameters (e.g., rate, AV Delay, V-V Delay, etc.) or anti-arrhythmia therapy parameters (e.g., timing, energy, leading edge voltage, etc.).

With respect to patient activity, an activity sensor may monitor diurnally to detect a low variance in a signal corresponding to a sleep state. For a complete description of an activity variance sensor, the reader is directed to U.S. Pat. No. 5,476,483 (Bornzin et al.), issued Dec. 19, 1995, which is hereby incorporated by reference.

The one or more physiological sensors 270 optionally include sensors for detecting movement and minute ventilation in the patient. Thus, the one or more physiologic sensors 270 may include a position sensor or a minute ventilation (MV) sensor to sense minute ventilation, which is defined as the total volume of air that moves in and out of a patient's lungs in a minute. Signals generated by a position sensor or MV sensor can be passed to the microcontroller 220 for analysis in determining whether to adjust the pacing rate, etc. The microcontroller 220 can monitor such signals for indications of the patient's position and activity status, such as whether the patient is climbing upstairs or descending downstairs or whether the patient is sitting up after lying down.

The stimulation device 100 optionally includes circuitry capable of sensing heart sounds or vibration associated with events that produce heart sounds. Such circuitry may include an accelerometer as conventionally used for patient position or activity determinations. Accelerometers typically include two or three sensors aligned along orthogonal axes. For example, a commercially available micro-electromechanical system (MEMS) marketed as the ADXL202 by Analog Devices, Inc. (Norwood, Mass.) has a mass of about 5 grams and a 14 lead CERPAK (approx. 10 mm by 10 mm by 5 mm or a volume of approx. 500 mm$^3$). The ADXL202 MEMS is a dual-axis accelerometer on a single monolithic integrated circuit and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL202 MEMS includes micro-circuitry and a mechanical oscillator.

While an accelerometer may be included in the case of an implantable pulse generator device, alternatively, an accelerometer communicates with such a device via a lead or through electrical signals conducted by body tissue or fluid. In the latter instance, the accelerometer may be positioned to advantageously sense vibrations associated with cardiac events. For example, an epicardial accelerometer may have improved signal to noise for cardiac events compared to an accelerometer housed in a case of an implanted pulse generator device.

The stimulation device 100 additionally includes a battery 276 that provides operating power to various circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 or to signal the microcontroller 220 that the external programmer 254 is in place to receive or transmit data to the microcontroller 220 through the telemetry circuits 264. Trigger IEGM storage also can be achieved by magnet.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds (HF indications—pulmonary edema and other factors); detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses in a range of joules, for example, conventionally up to about 40 J, as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), or synchronized with an R-wave or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In low-energy cardioversion, an ICD device typically delivers a cardioversion stimulus (e.g., 0.1 J, etc.) synchronously with a QRS complex; thus, avoiding the vulnerable period of the T wave and avoiding an increased risk of initiation of VF. In general, if antitachycardia pacing (ATP) therapy or cardioversion therapy fails to terminate a tachycardia, then, for example, after a programmed time interval or if the tachycardia accelerates, the ICD device may initiate defibrillation therapy.

While an ICD device may reserve defibrillation as a latter tier therapy, it may use defibrillation as a first-tier therapy for VF or other conditions. In general, an ICD device does not synchronize defibrillation therapy with any given portion of an ECG. Again, defibrillation therapy typically involves high-energy shocks (e.g., 5 J to 40 J), which can include monophasic or unidirectional or biphasic or bidirectional shock waveforms (or other forms). Defibrillation may also include delivery of pulses over two current pathways.

Ventricular Arrhythmias

Ventricular arrhythmias are a leading cause of sudden cardiac death; thus, detection and treatment ventricular arrhythmias or precursors thereto can help prevent such deaths. Ventricular arrhythmias may arise from any of a variety of conditions including hemodynamic conditions such as myocardial ischemia. For example, localized ischemia may alter responsiveness of a myocardial region and, in turn, a ventricular arrhythmia may develop having a reentry wavefront or circuit that travels around the unresponsive region. Of course global ischemia may initiate ventricular arrhythmias as well. Whether global or local, knowledge of an arrhythmia's spatial characteristics can improve treatment. Further, knowledge of an ischemia's spatial characteristics can be beneficial for detection or treatment as well.

With respect to anti-arrhythmia therapies that account for spatial characteristics, some studies suggest pacing or delivering stimulation at a site where the site position is selected based on the spatial location of a reentry circuit. For example, pacing or delivering may occur at a site proximate to a reentry circuit or at a site removed from a reentry circuit. Of course, for some patients pacing or delivering is limited to a single site; consider, for example, an implantable cardiac device having a single lead with a pacing electrode positioned in a patient's right ventricle. In such instances, spatial information may prove beneficial, for example, in determining a pacing time or pacing amplitude, frequency, etc.

Various factors can affect successful termination of a ventricular arrhythmia. Such factors include, but are not limited to, arrhythmia rate (e.g., path length and conduction velocity), refractory period at a pacing or stimulation site or in a reentry circuit, conduction path from pacing or stimulation site to a reentry circuit (e.g., including conduction velocity, conduction time, etc.), reentry circuit gap characteristics. See, e.g., Sinha, et al., "Critical role of inhomogeneities in pacing termination of cardiac reentry", CHAOS, 12(3): 893-902 (2002). As described herein, anti-arrhythmia therapy is optionally based on spatial information where the spatial information may indicate whether an arrhythmia is local or global, whether ischemia is local or global, etc. Further, detection of an arrhythmia or precursor thereto may rely on spatial information.

While spatial information can be useful for detection or treatment of arrhythmias, temporal information can help as well. Consider FIG. 3, which shows electrical cardiac waveforms of an exemplary progression of worsening cardiac condition 300. While the particular progression shown may vary in form, scale, etc., it represents a natural and untreated progression of worsening cardiac condition (see, e.g., Weiss et al., "Ventricular Fibrillation: How Do We Stop the Waves From Breaking?", Circ Res. 2000; 87:1103-1107).

Figure 3:
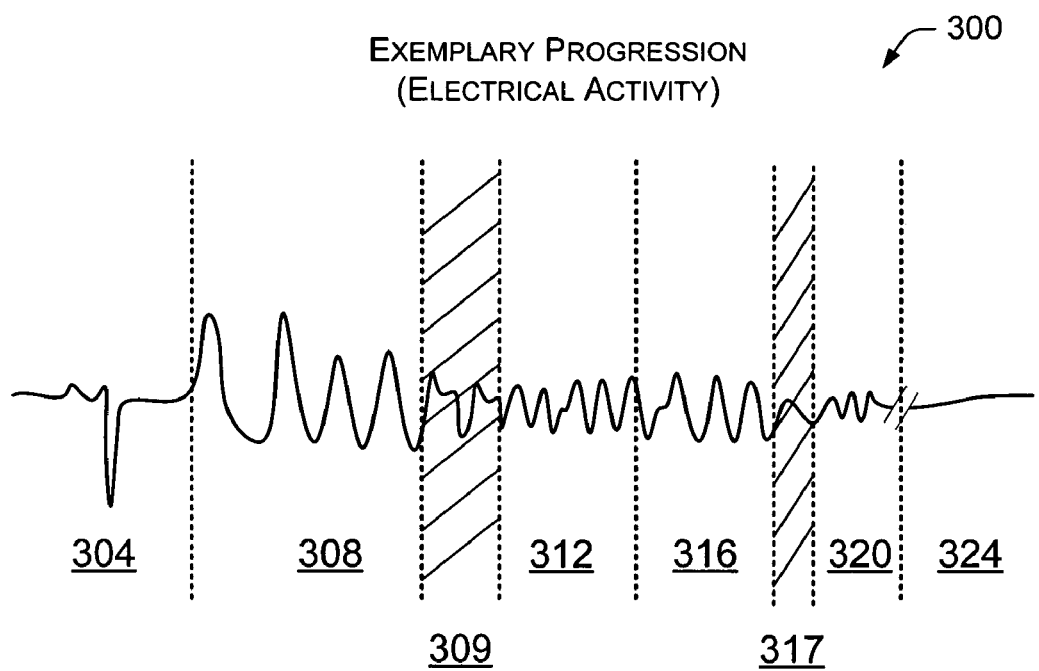
FIG. 3 is a diagram of an exemplary progression of cardiac activity from normal to asystolic.

In FIG. 3, various vertical dashed lines separate or designate regions of the progression 300. The regions include a normal sinus region 304 (e.g., one main event), a region 308 of early organized activation having at least some characteristics associated with or indicative of ventricular tachycardia (e.g., about four events), a transition region 309 of more complex morphology and typically a decreased interval that may be associated with or indicative of ventricular fibrillation (VF), an early, coarse ventricular fibrillation (VF) region 312, a later, coarse ventricular fibrillation (VF) region 316 (e.g., may be observed in ischemia induced arrhythmia onset), a coarse to fine ventricular fibrillation (VF) region 317, a fine ventricular fibrillation (VF) region 320 and an asystole region 324.

While the exemplary progression 300 is shown with electrical cardiac waveforms, a similar progression may be noted using other signals. For example, a hemodynamic sensor may detect hemodynamic behavior that indicates compromised cardiac performance. FIG. 2, described above, shows an exemplary device that optionally includes one or more physiologic sensors 270, which may include a hemodynamic sensor or other sensors for detecting arrhythmias or precursors thereto. Such sensors may provide spatial information as well.

Figure 4:
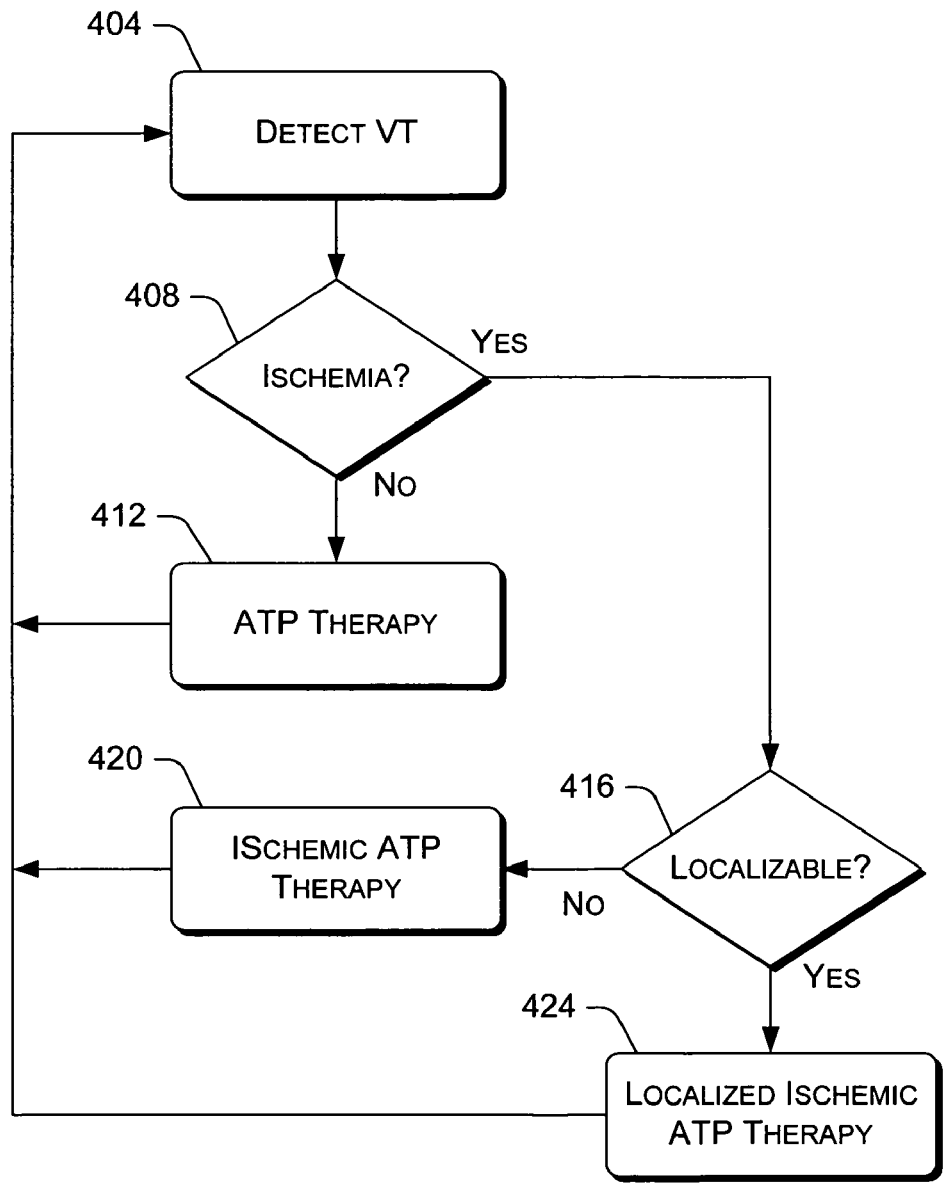
FIG. 4 is an exemplary method for detecting ventricular tachycardia and ischemia, if present, and then determining an appropriate anti-tachycardia therapy in response to the detections.

FIG. 4 shows an exemplary method 400 for treating ventricular tachycardia (VT). The method 400 commences in a detection block 404 which detects VT. A decision block 408 follows that decides if ischemia exists. If ischemia does not exist, then a delivery block 412 delivers conventional anti-tachycardia pacing (ATP) therapy. However, if ischemia exists, then the method 400 continues in another decision block 416 that decides if the ischemia is localizable. If the ischemia is not localizable, for example, global ischemia, then the method 400 continues in a delivery block 420 that delivers ATP therapy based at least in part on the presence of a non-localizable ischemia. However, if the ischemia is localizable, then the method 400 continues in a delivery block 424 that delivers ATP therapy based at least in part on the presence of a localized ischemia.

As described, the exemplary method 400 selects an ATP therapy based at least in part on existence of ischemia and whether such ischemia is localizable or not. As already mentioned, ventricular tachyarrhythmia or tachycardia may arise from ischemia. In such instances, ATP therapy accounts for reduced blood flow to the myocardium. In instances where spatial information can help localize ischemia, then ATP therapy accounts for location of the ischemia.

Therapies delivered in the exemplary method 400 may be selected on the basis of testing. For example, a balloon catheter may be used to cause global ischemia that, in turn, causes VT. Spatial or temporal characteristics of the VT may be noted (e.g., via electrical, hemodynamic or other sensors) and treatment selected on the basis of such characteristics. Global ischemia may cause global VT or local VT. In instances where global ischemia causes VT localized predominantly in the right ventricle, electrodes may be selected to deliver ATP therapy to the right ventricle. In instances where global ischemia causes a more global VT, then electrodes may be selected to deliver a more global ATP therapy (e.g., can electrode and RV-tip electrode, etc.). Such a therapy may be delivered via the delivery block 420 of FIG. 4.

The process described above for causing global ischemia may be used to cause local ischemia. For example, a balloon catheter may be inserted in a coronary vein or artery to reduce blood flow to a particular myocardial region. In turn, spatial or temporal information may be acquired to determine spatial or temporal characteristics of any resulting VT. Where a variety of electrode configurations are available, ATP therapy can be delivered using one or more of the configurations to determine which configuration(s) exhibit a higher probability of success in terminating the VT. Such a therapy may be delivered via the delivery block 424 of FIG. 4.

Figure 5:
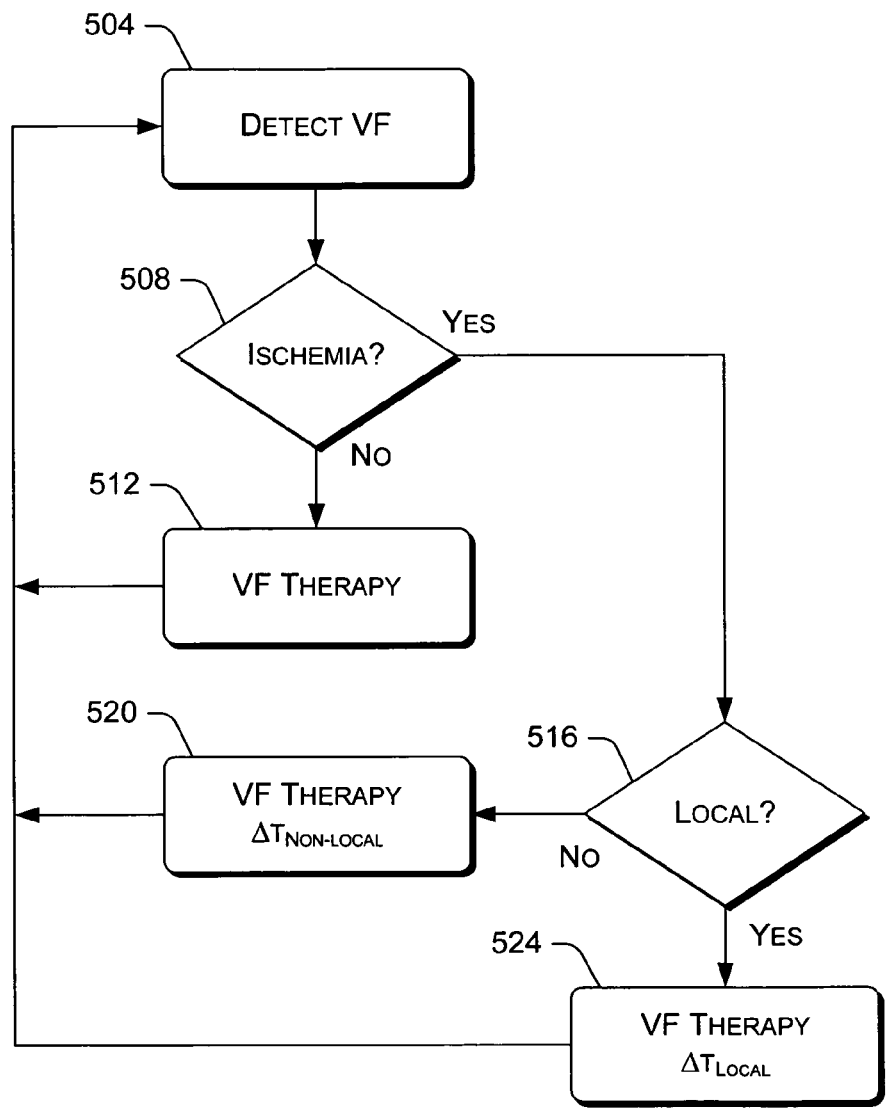
FIG. 5 is an exemplary method for detecting ventricular fibrillation and ischemia, if present, and then determining an appropriate defibrillation therapy in response to the detections.

FIG. 5 shows an exemplary method 500 for treating ventricular fibrillation (VF). The method 500 commences in a detection block 504 which detects VF. A decision block 508 follows that decides if ischemia exists. If ischemia does not exist, then a delivery block 512 delivers conventional VF therapy. However, if ischemia exists, then the method 500 continues in another decision block 516 that decides if the ischemia is local. If the ischemia is not local, for example, global ischemia, then the method 500 continues in a delivery block 520 that delivers VF therapy based at least in part on the presence of a non-local or global ischemia. However, if the ischemia is local, then the method 500 continues in a delivery block 524 that delivers VF therapy based at least in part on the presence of a local ischemia.

As described, the exemplary method 500 selects a VF therapy based at least in part on existence of ischemia and whether such ischemia is local or not. As already mentioned, VF may arise from ischemia. In such instances, VF therapy accounts for reduced blood flow to the myocardium. In instances where spatial information can help localize the ischemia, then VF therapy may account for location of the ischemia.

With respect to VF therapies, if a method calls for and delivers about 5 to about 7 defibrillation shocks (e.g., a programmed limit on the number of successive shocks) and the patient has not collapsed, then the detection or diagnosis was in error and no more shocks should be delivered. However, if a patient is experiencing VF dues to an ischemic attack (or infarction), then delivery of defibrillation shocks should continue regardless of the cost in terms of patient pain or depletion of an implantable device's energy.

In the instance that a local ischemia has caused the VF (e.g., the VF appears to be confined to a region around one lead), then a reasonable assumption is that there is a new infarct which is causing the cardiac instability that is causing VF. In response, an exemplary method may call for delivery of one shock every 20 seconds (i.e., a shock-to-shock timing $\Delta T_{Local}$) without a limit as to number of successive shocks or with an increased limit ($N_{Local}$) (e.g., consider the delivery block 524). Such an approach contrasts with a conventional approach that simply delivers shocks about every 6 seconds, which may merely deplete the battery without solving consequences of an ongoing local ischemia.

However, if ischemia appears to be global, then the exemplary method 500 may consider VF as a cause of the ischemia and that the VF is of a fairly late stage (e.g., consider stage 320 of FIG. 3). Further, since the heart is in VF, an electrogram is unlikely to have much utility for the detection of ischemia and thus ischemia detection can rely on use of other sensors. In the case of global ischemia and late stage VF, the exemplary method 500 may deliver shocks as rapidly as possible (e.g., a short shock-to-shock timing, $\Delta T_{Global} < \Delta T_{Local}$) without limit (e.g., $N_{Global}$ set to a sufficiently high number, $N_{Global} >> N_{Local}$) as to the number of consecutive shocks (e.g., consider the delivery block 520).

Table 1 below summarizes various exemplary approaches to treatment of VT or VF based on ischemia and spatial information. Table 1 includes a shock-to-shock timing parameter $\Delta T$ and a limit as to number of successive shocks N. In general, $\Delta T_{Local}$ is less than $\Delta T_{Global}$ and $N_{Local}$ much less than $N_{Global}$.

TABLE 1

Exemplary Approaches to Treatment

|  | VT | VF |
|---|---|---|
| No Ischemia | ATP | Defib Shock |
| Local Ischemia | Local ATP | $\Delta T_{Local}, N_{Local}$ |
| Global Ischemia | Global ATP | $\Delta T_{Global}, N_{Global}$ |

An exemplary method includes detecting arrhythmia, determining whether myocardial ischemia exists and, in response to the determining, calling for delivery of either an ischemic anti-arrhythmia therapy or a non-ischemic anti-arrhythmia therapy. Such an exemplary method may rely on a table such as Table 1 to call for appropriate therapy based on whether ischemia exists or, for example, whether ischemia is local or global.

With respect to differences between ischemic anti-arrhythmia therapy and non-ischemic anti-arrhythmia therapy, consider VT storm, which may persist for minutes or longer. If ischemia exists, then such an exemplary method may call for more oversight of resources, for example, by lengthening the duration between successive calls for anti-arrhythmia therapy should the therapy fail to abate the VT storm. A particular ischemic anti-arrhythmia therapy includes repeatedly calling for delivery of anti-arrhythmia therapy wherein the duration between the calls or the deliveries is greater than approximately 10 seconds. In contrast, a non-ischemic anti-arrhythmia therapy responsive to VT storm may include repeatedly calling for delivery of anti-arrhythmia therapy wherein the duration between the calls or the deliveries is approximately 10 seconds or less. Of course, severity or locality of ischemia may affect choice of therapy.

Consider treatment of VF as another example. If acute ischemia exists together with VF, a call may be made for therapy that increases spacing between shocks and use higher shocks. Such a strategy can act to stretch out delivery of therapy over about 5 minutes whereas a standard therapy may call for delivery of shocks about every 10 seconds for about 1 minute. Anti-arrhythmia therapy for ischemia, may include modification of a waveform parameter to account for an increased membrane time constant, as commonly associated with ischemia. With respect to localization of therapy, a border zone may be targeted.

As already mentioned, ischemia information may be acquired via any of a variety of sensors or electrodes. With respect to sensing temperature, various studies recognize that coronary sinus blood temperature increases upon decreased coronary blood flow. For example, a study by Stefanadis et al., "The cooling effect of coronary blood flow on heart: a new approach", J Invasive Cardiol. 2004 September; 16(9): 455-8, noted that coronary sinus blood temperature increased during interruption of coronary blood flow with balloon dilatation. In particular, the study calculated the difference between blood temperature in the coronary sinus and right atrium during and after acute occlusion of blood flow in the left coronary artery. Another study by Stefanadis et al., "Temperature of blood in the coronary sinus and right atrium in patients with and without coronary artery disease", noted that coronary sinus temperature was increased in patients with coronary artery disease compared with a control group and was found to be a prognostic factor for mid-term clinical outcome. Thus, the cooling effect of blood flow through the heart has been established and where blood flow decreases, the temperature of venous coronary blood increases. Consequently, an increase in venous coronary blood temperature can be due to ischemia.

Figure 6:
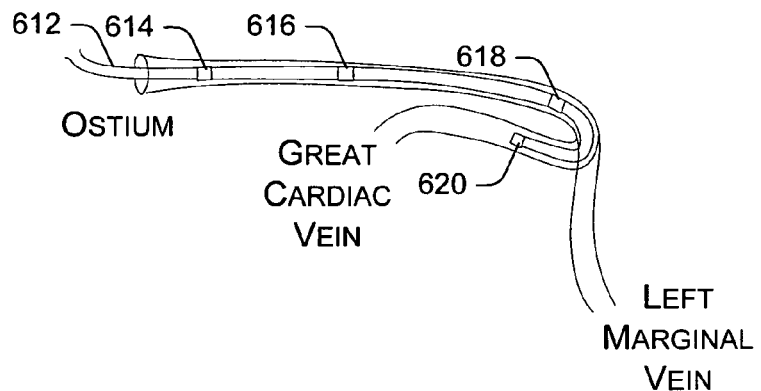
FIG. 6 is a diagram of a coronary sinus temperature sensing lead and a diagram of various exemplary measurement locations in the coronary sinus or tributaries thereto.
Figure 6:
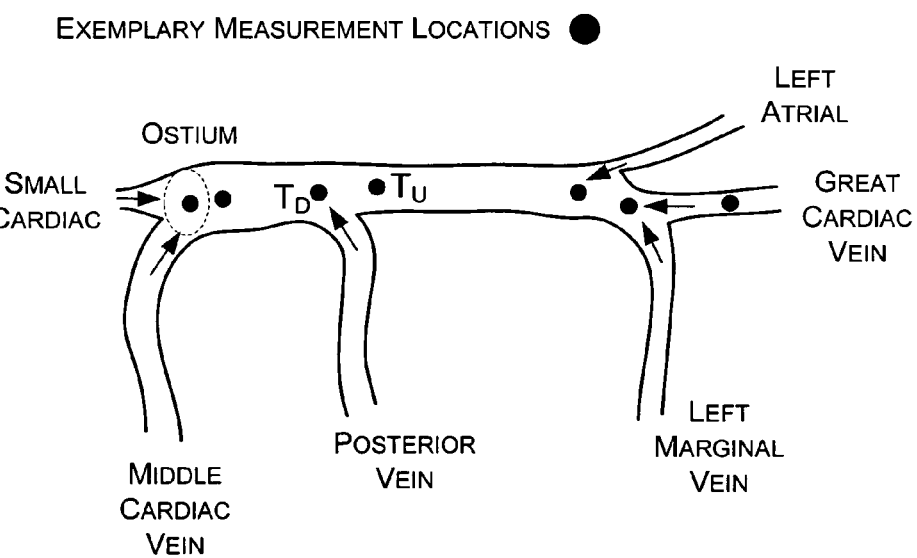

Published US Patent Application 20050004476 to Payvar (Payvar application) discloses a coronary sinus lead having four temperature sensors, which is reproduced in FIG. 6 as lead 610. The lead 610 includes a lead body 612 and four temperature sensors 614, 616, 618 and 620. The Payvar application notes that the occurrence of a temperature gradient indicative of ischemia in a subset of these sensors will correspond to the origin of a certain vein draining to the coronary sinus, thereby determining the area in which ischemia has occurred, or been more functionally pronounced.

To more fully appreciate how a temperature sensor array in the coronary sinus or tributaries thereof can provide information as to ischemia and whether such ischemia is local or global, consider the diagram 640 of FIG. 6, which shows a more detailed anatomical view together with exemplary measurement locations. Given the cooling effect of blood and basic hydrodynamics, if one coronary flow path is to some degree occluded then flow through this path will decrease and temperature of blood in this path will increase while flow is likely to be diverted via other flow paths of lesser resistance. To predict a priori whether a particular tributary to the coronary sinus will increase coronary sinus temperature depends primarily on heat flow, which is the product of temperature and mass flow. As mass flow decreases along a coronary flow path, temperature of the blood increases. Consequently, for a decrease in mass flow, heat flow for this path may remain constant, increase or decrease.

Consider two flow paths where in a first path blood flows at a mass flow of $m_1$ and at a temperature $T_1$ and in a second path blood flows at a mass flow of $m_2$ and at a temperature $T_2$. Upon confluence, the total heat flow is $C_b(m_1 T_1 + m_2 T_2)$, where $C_b$ is the heat capacity of blood. If the first and second paths are supplied by a common source, then an increase in resistance in one path is likely to lead to an increase in mass flow through the other path; however, total mass flow will remain essentially constant. Further, blood flowing through the non-occluded path may increase in temperature or decrease in temperature. Consequently, a simple occurrence of a temperature gradient in a subset of the sensors of the lead 610 may not help localize ischemia. Thus, the following exemplary method is proposed to help localize ischemia.

If the posterior vein is taken as a first flow path and a point just upstream of the confluence of the posterior vein (PV) in the coronary sinus is taken as a second flow path, then two temperature measurement points are of interest: a temperature measurement point upstream ($T_U$) of the confluence and a temperature measurement point at or just downstream ($T_D$) of the confluence. The temperature $T_U$ will depend on the heat flow from tributaries upstream while the temperature $T_D$ will depend on those tributaries plus the contribution from the posterior vein, hence a change in $T_U$ will affect $T_D$, as will a change in mass flow upstream $m_U$. The following equations help summarize this scenario: $Q_U = C_b m_U T_U$; $T_U = Q_U/C_b m_U$; $Q_D = C_b m_U T_U + C_b m_{PV} T_{PV} = C_b m_D T_D$; and $T_D = (m_U T_U + m_{PV} T_{PV})/m_D = Q_D/C_b m_D$.

In the case of ischemia related to the posterior vein, $T_{PV}$ will increase and $m_{PV}$ will decrease, whereas, if ischemia is upstream of the confluence, then $T_U$ may increase and $m_U$ may decrease. Thus, a temperature gradient at any given time will not necessarily help to localize ischemia. Instead, an exemplary method includes tracking temperatures or temperature gradients over time. For example, if in the aforementioned example, $\Delta T$ is calculated as $T_U - T_D$ and $\Delta T$ changes over time, then further investigation is warranted. In general, if $T_D$ increases over time while $T_U$ remains fairly constant, then it is likely that ischemia is associated with a flow path that includes the posterior vein. If $\Delta T$ is calculated as $T_U - T_D$, then a decreasing $\Delta T$ would reflect this scenario. For assurance, an exemplary method includes tracking an upstream temperature, a downstream temperature and a temperature difference over time to help determine if ischemia is local and, if so, to help localize the ischemia.

Figure 7:
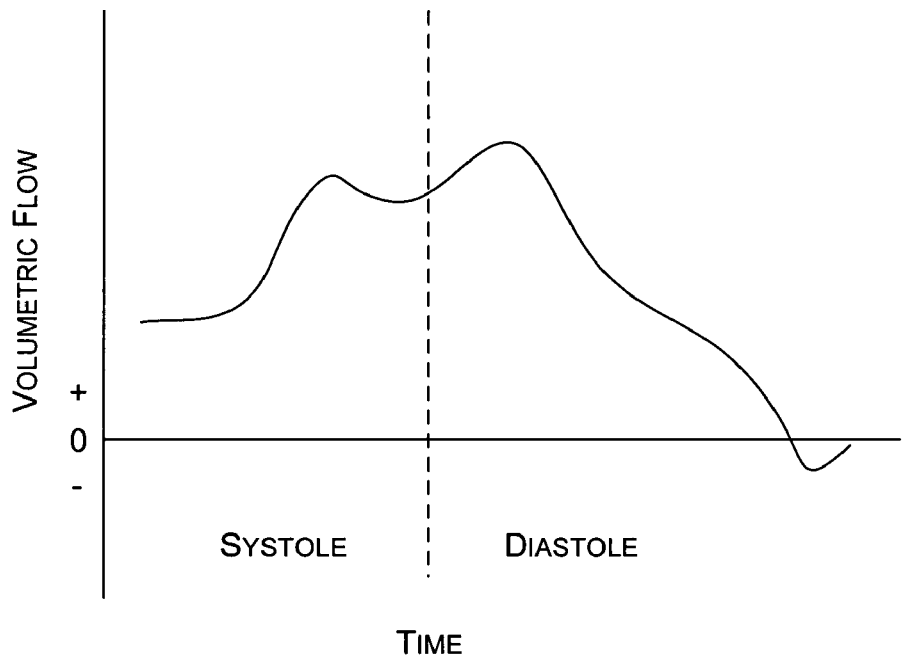
FIG. 7 is an exemplary plot of coronary sinus flow versus time and an exemplary measurement timing sequence for measuring coronary sinus flow.
Figure 7:
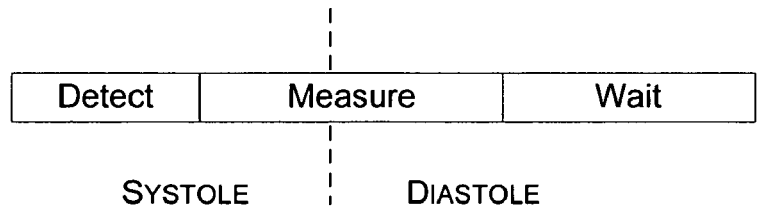

Flow in the coronary sinus varies with respect to time and, in particular, with respect to cardiac cycle phase. FIG. 7 shows an exemplary plot of coronary sinus flow versus time 710 and an exemplary measurement timing sequence 740. The volumetric flow or mass flow of blood in the coronary sinus is predominantly positive toward the ostium of the right atrium. However, in late diastole, negative flow may occur from the right atrium to the coronary sinus.

As the flow of blood from the right atrium may affect measurements in the coronary sinus, an exemplary timing sequence 740 includes detecting a R-wave, detecting a QRS complex, detecting an evoked response or noting a pacing event and then acquiring one or more measurements in the coronary sinus during an acquisition window. The duration of the acquisition window may extend from mid- to late systole to early to mid-diastole, where volumetric flow in the coronary sinus is at or near maximum. Such a timing sequence may help to avoid spurious measurements, for example, measurements that are more indicative of coronary sinus wall temperature than venous blood temperature. As the coronary sinus is quite flexible, during low flow, the walls may collapse and thereby affect temperature or temperature measurement. Again, it is the blood flowing from various regions of the heart that carry information regarding ischemia; thus, measurements during expected high coronary sinus flow are likely to more accurately reflect ischemia.

Where temperatures approaching wall temperatures are of interest, a timing sequence may include an acquisition window during times of expected low volumetric or mass flow. Such temperatures may be used in conjunction with higher flow temperatures to determine heart condition.

With respect to pacing, temperature measurements or other measurements may provide information as to effectiveness of pacing. For example, where pacing increases the temperature of blood in the coronary sinus, the pacing may be causing the heart to work in a manner that increases heat generation by a suboptimal transventricular timing. Such information may be used to select or adjust pacing parameters.

While various examples focus on temperature, other parameters may be used to detect or to help localize ischemia. For example, FIG. 8 includes a table 810 of exemplary parameters (e.g., temperature, $O_2$, pH, dV/dt, Pressure) and locations of sensors (e.g., GCV, LMV, MCV, PV, LAV, ostium, CS, RV, IVC, SVC). The locations may correspond to a sensor positioned in the lumen of a tributary or to a confluence of the tributary with another vein or venous structure (e.g., the coronary sinus).

Figure 8:
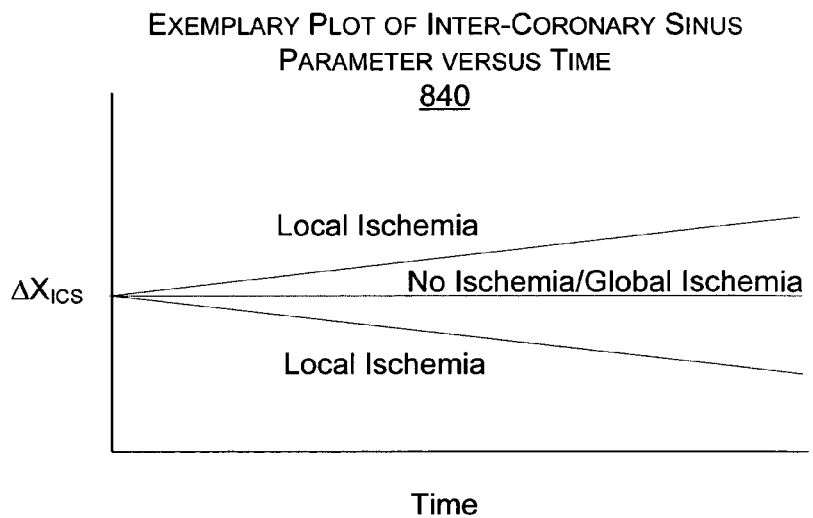
FIG. 8 is a table of various exemplary parameters and an exemplary plot of a parameter difference with respect to time for aiding in diagnosing local or global ischemia.

FIG. 8 also shows an exemplary plot 840 of an inter-coronary sinus parameter difference versus time. The parameter may be selected from the table 810 or from other parameters. In general, a change in an inter-coronary sinus parameter difference versus time can be an indicator of ischemia and may help to localize ischemia.

Figure 9:
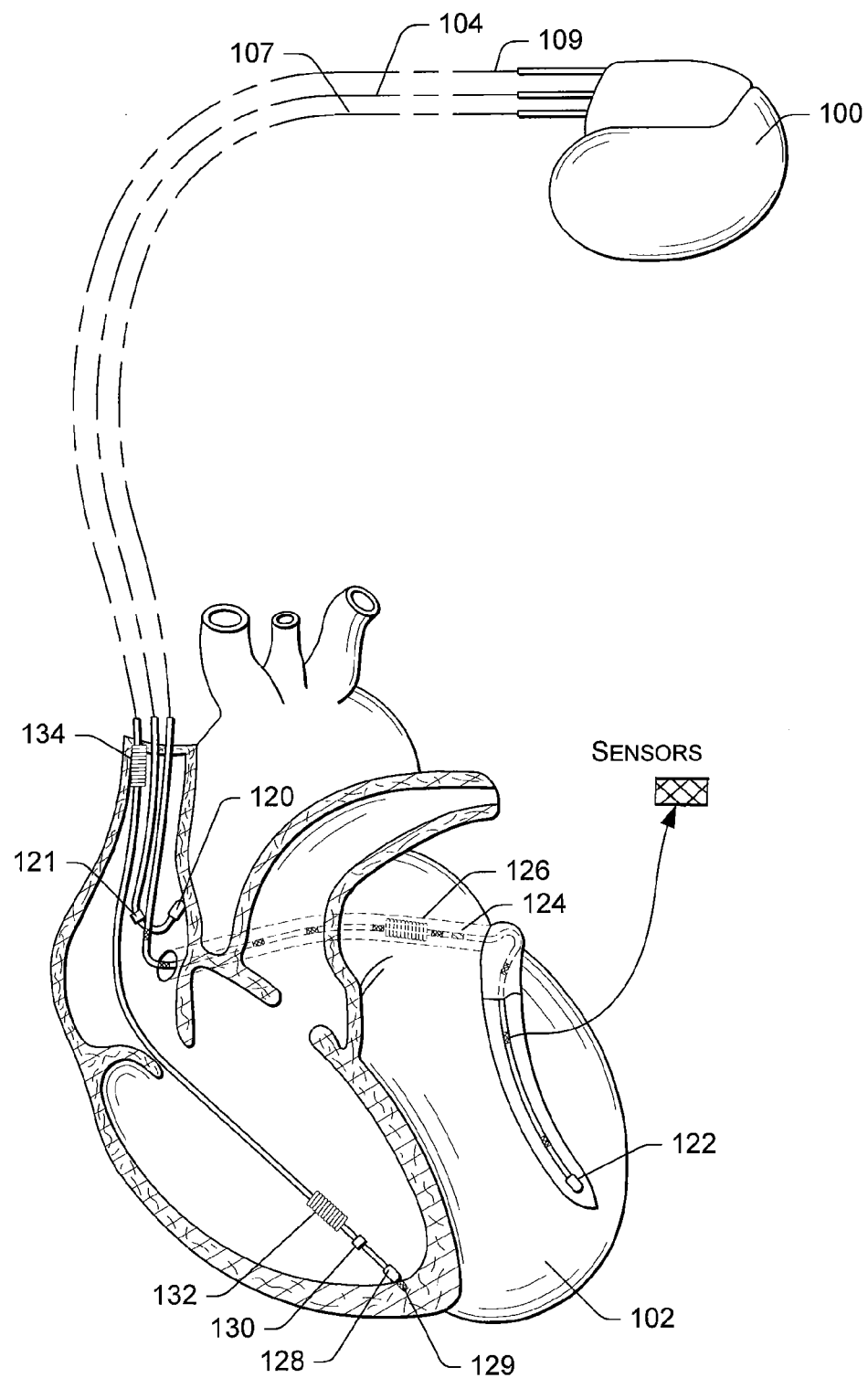
FIG. 9 is a diagram of a heart, an implantable device and various exemplary leads that include sensors for sensing information related to ischemia.

FIG. 9 shows the exemplary arrangement of FIG. 1 where the leads 106 and 108 have been replaced with specialized leads 107 and 109, which include one or more sensors for sensing information related to ischemia or to localization of ischemia. The specialized leads 107 and 109 can retain the functionality described above with respect to the leads 106 and 108 while having additional capabilities. With respect to the lead 107, a tip sensor 129 is positioned in the right ventricular wall. The tip sensor 129 may sense temperature or another parameter. Published US Patent Application 20050004476 to Payvar (Payvar application), discloses that the temperature of the myocardium of the apex, unlike that of the temperature in the coronary sinus, decreases during ischemia. Thus, the tip sensor 129 may sense temperature of the myocardium proximate to the apex. An exemplary method may use such information to determine whether ischemia exists or to help localize ischemia. Further, such information may be used in conjunction with other information, such as information acquired in a coronary vein or venous structure.

An exemplary method optionally includes use of a differential temperature measurement. For example, a coronary sinus temperature and an apex temperature (e.g., right atrial lead-based tip sensor) may be used to acquire a differential temperature.

The specialized lead 109 includes a plurality of sensors that may be positioned at locations in the superior vena cava to one or more coronary veins (for example, where legs or branches exist). The plurality of sensors may acquire temperature or other information for use in determining whether ischemia exists or to help localize ischemia.

Figure 10:
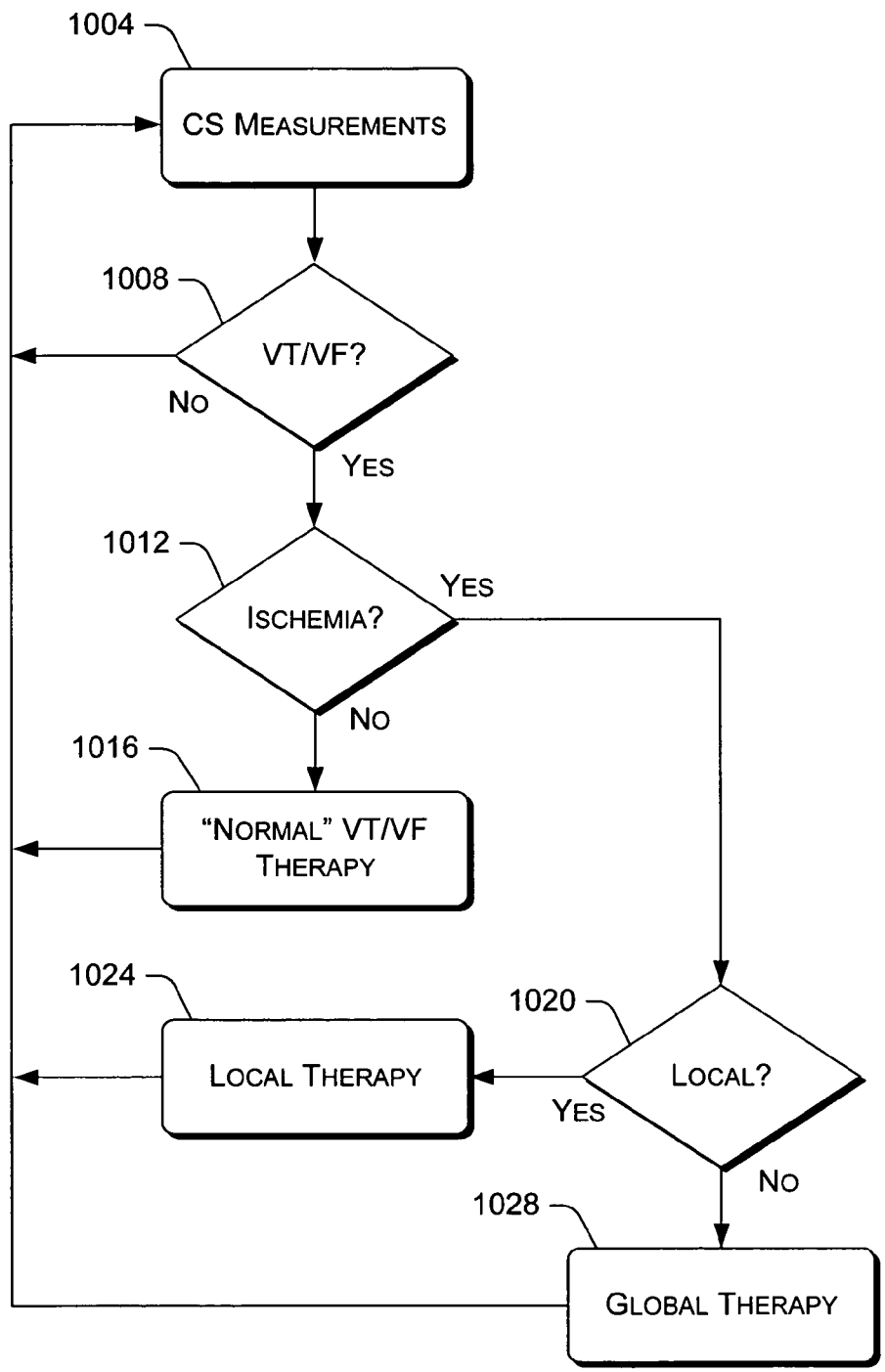
FIG. 10 is an exemplary method for detecting arrhythmia and ischemia information based at least in part on measurements in the coronary sinus or tributaries thereto.

FIG. 10 shows an exemplary method 1000 that relies on coronary sinus or other coronary vein measurements to detect arrhythmia and whether ischemia exists. Published US Patent Application 20050004476 to Payvar (Payvar application), discloses that the temperature in the coronary sinus varies during the cardiac cycle. Such variation is likely related to the cooling effect of blood and the variation in flow of blood in the coronary sinus (see, e.g., the plot 710 of FIG. 7). The Payvar application also discloses the possibility of detecting heart rhythm abnormalities in the course of the study of a coronary sinus temperature wave form.

The exemplary method 1000 commences in a coronary sinus measurement block 1004 where one or more sensors acquire information related to blood or blood flow in the coronary sinus. One or more sensors may also be positioned in other coronary veins (e.g., tributaries to the coronary sinus) or other locations. The method 1000 continues in a decision block 1008 that decides, based at least in part on the acquired information, if an arrhythmia exists (e.g., a VT or VF). If not, then the method 1000 continues at the measurement block 1004. However, if the decision block 1008 decides that an arrhythmia exists, then the method 1000 enters another decision block 1012 that decides, based at least in part on the acquired information, if ischemia exists.

If ischemia does not exist, then the method 1000 continues in a delivery block 1016 that delivers conventional VT or VF therapy. In the case that ischemia does exist, however, the method 1000 continues in yet another decision block 1020 that decides if the ischemia is local. If the ischemia is local, then a delivery block 1024 delivers local therapy to treat the VT or VF; whereas, if the ischemia is not local, then a delivery block 1028 delivers global therapy to treat the VT or VF. Therapies are optionally selected based on the examples of Table 1, above.

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed:

1. A method comprising:
    detecting an arrhythmia;
    determining whether myocardial ischemia exists;
    if myocardial ischemia exists, determining whether the ischemia is local or global;
    if the ischemia is local, delivering a therapy comprising a first number of successive shocks separated by a first shock-to-shock time;
    if the ischemia is global, delivering a therapy comprising a second number of successive shocks separated by a second shock-to-shock time, wherein the second number of successive shocks is greater than the first number of successive shocks and the second shock-to-shock time is greater than the first shock to shock time.

2. The method of claim 1 wherein determining whether myocardial ischemia exists comprises using information related to blood or blood flow in the coronary sinus or a tributary thereof.

3. The method of claim 2 wherein the information comprises temperatures information.

4. The method of claim 1 wherein determining whether myocardial ischemia exists comprises using a blood temperature difference.

5. The method of claim 1 wherein determining whether myocardial ischemia exists comprises using a coronary sinus blood temperature.

6. An implantable apparatus comprising:
    a processor;
    a circuit configured to acquire information related to blood or blood flow in the coronary sinus or a tributary thereof; and
    control logic configured to detect an arrhythmia, to determine whether local myocardial ischemia or global myocardial ischemia exists based at least in part on the information, and to call for delivery of a local ischemic anti-arrhythmia therapy comprising a first number of successive shocks separated by a first shock-to-shock time or a global ischemic anti-arrhythmia therapy comprising a second number of successive shocks separated by a second shock-to-shock time, wherein the second number of successive shocks is greater than the first number of successive shocks and the second shock-to-shock time is greater than the first shock to shock time.

* * * * *